United States Patent
Nadeau et al.

(10) Patent No.: US 9,533,134 B2
(45) Date of Patent: Jan. 3, 2017

(54) SILICONE TUBING AND METHOD FOR MAKING AND USING SAME

(71) Applicants: Adam P. Nadeau, Hudson, MA (US); Michael E. Cahill, Waunakee, WI (US); Michael J. Tzivanis, Chicopee, MA (US); Ashok Mohanty, Marlborough, MA (US)

(72) Inventors: Adam P. Nadeau, Hudson, MA (US); Michael E. Cahill, Waunakee, WI (US); Michael J. Tzivanis, Chicopee, MA (US); Ashok Mohanty, Marlborough, MA (US)

(73) Assignee: SAINT-GOBAIN PERFORMANCE PLASTICS CORPORATION, Solon, OH (US)

( * ) Notice: Subject to any disclaimer, the term of this patent is extended or adjusted under 35 U.S.C. 154(b) by 506 days.

(21) Appl. No.: 13/865,934

(22) Filed: Apr. 18, 2013

(65) Prior Publication Data

US 2013/0302548 A1    Nov. 14, 2013

Related U.S. Application Data

(60) Provisional application No. 61/625,998, filed on Apr. 18, 2012.

(51) Int. Cl.
*A61M 39/08*    (2006.01)
*B29C 47/00*    (2006.01)
(Continued)

(52) U.S. Cl.
CPC .......... *A61M 39/08* (2013.01); *B29C 47/0004* (2013.01); *F16L 11/06* (2013.01);
(Continued)

(58) Field of Classification Search
CPC   A61M 39/08; B29C 47/0004; B29C 47/0023;
B29C 47/0076; B29C 47/367; B29C
2947/92019; B29C 2947/92123; B29C
2947/9238; B29C 2947/92428; B29C
2947/9259; B29C 2947/926; B29C
2947/92704; B29C 2947/92876; B29C
2947/92619; B29K 2083/00; F16L 11/06
See application file for complete search history.

(56) References Cited

U.S. PATENT DOCUMENTS 4,882,101 A    11/1989 Ohkita et al.
5,059,363 A    10/1991 Davis et al.
(Continued)

FOREIGN PATENT DOCUMENTS

CN    86106778 A    4/1988
CN    2079249 U    6/1991
(Continued)

OTHER PUBLICATIONS

International Search Report for PCT/US2013/037244 dated Jul. 22, 2013, 4 pgs.
(Continued)

*Primary Examiner* — Michael C Miggins
(74) *Attorney, Agent, or Firm* — Abel Law Group, LLP; Chi Suk Kim (57) ABSTRACT

Silicone tube structures are formed having a particular dimensional accuracy. In one embodiment, a silicone tube structure can include an extruded hollow body having an inner bore. The extruded hollow body can have an inner diameter, an outer diameter, and a length of at least approximately 20 m. The extruded hollow body can also have a dimensional accuracy that is measured by the standard deviation of the inner diameter being no greater than approximately 0.8% of an average inner diameter of the extruded hollow body over the length. In an embodiment,
(Continued)

the silicone tube structure can be cut to form a number of silicone tubes.

20 Claims, 5 Drawing Sheets

(51) Int. Cl.
  *F16L 11/06* (2006.01)
  *B29C 47/36* (2006.01)
  *B29K 83/00* (2006.01)

(52) U.S. Cl.
  CPC ...... *B29C 47/0023* (2013.01); *B29C 47/0076* (2013.01); *B29C 47/367* (2013.01); *B29C 2947/926* (2013.01); *B29C 2947/92019* (2013.01); *B29C 2947/9238* (2013.01); *B29C 2947/9259* (2013.01); *B29C 2947/92123* (2013.01); *B29C 2947/92428* (2013.01); *B29C 2947/92619* (2013.01); *B29C 2947/92704* (2013.01); *B29C 2947/92876* (2013.01); *B29K 2083/00* (2013.01); *Y10T 428/139* (2015.01)

(56) References Cited

U.S. PATENT DOCUMENTS

| | | |
|---|---|---|
| 5,246,752 A | 9/1993 | Raczkowski |
| 5,759,647 A | 6/1998 | Kuroda et al. |
| 5,820,607 A | 10/1998 | Tcholakian et al. |
| 5,948,332 A | 9/1999 | Prenger |
| 6,508,972 B1 | 1/2003 | Lietz |
| 2001/0022411 A1 | 9/2001 | Conway et al. |
| 2003/0030165 A1 | 2/2003 | Centell et al. |
| 2003/0132552 A1 | 7/2003 | Gamble et al. |
| 2006/0255497 A1 | 11/2006 | Prevotat |
| 2008/0166509 A1 | 7/2008 | Simon et al. |
| 2008/0248226 A1 | 10/2008 | Simon et al. |
| 2011/0005661 A1 | 1/2011 | Brustad et al. |

FOREIGN PATENT DOCUMENTS

| | | |
|---|---|---|
| CN | 2226602 Y | 5/1996 |
| EP | 2062605 A1 | 5/2009 |
| JP | S55-140542 A1 | 11/1980 |
| WO | 2013158927 A1 | 10/2013 |

OTHER PUBLICATIONS

Supplemental Search Report for EP13778858 dated Jan. 25, 2016, 1 pg.

SILICONE TUBING AND METHOD FOR MAKING AND USING SAME

CROSS-REFERENCE TO RELATED APPLICATION

The present application claims priority from U.S. Provisional Patent Application No. 61/625,998 entitled "Silicone Tubing and Method for Making and Using Same," by Adam P. Nadeau, Michael E. Cahill, Michael J. Tzivanis, and Ashok Mohanty filed Apr. 13, 2012, which is incorporated by reference herein in its entirety.

BACKGROUND

Many industries utilize tubing to dispense fluid or remove fluid. For example, in the medical industry, tubing is used to deliver fluid containing nutrients or medication to patients. Tubing can also be used in medical applications to remove fluid from patients and to drain fluid produced during some procedures. In certain applications, a specified amount of fluid is expected to be delivered or removed over a particular period of time.

In many cases, the medical and pharmaceutical industries utilize silicone tubing for the delivery and removal of fluids because silicone tubing is non-toxic, flexible, thermally stable, has low chemical reactivity, and can be produced in a variety of sizes when compared with tubing made from other materials. For example, silicone tubing may be used with enteral pumps and infusion pumps to provide nutrients, medication, fluids, and the like to patients.

Medical devices utilizing silicone tubing are expected to deliver or remove fluids at a specified rate. To illustrate, an enteral pump can be expected to deliver a selected amount of nutritional fluid to a patient in a particular period of time, such as 50 mL/hour. The dimensions of the silicone tubing coupled to medical devices can affect the flow rate of fluid pumped by the devices. Consequently, medical and pharmaceutical industries would benefit from cost effective tubing solutions that provide a high level of dimensional accuracy.

Typically, silicone tubing is formed by one of two processes, extrusion or molding. During extrusion, a flowable raw material is forced through a die and is then solidified. Existing extrusion processes have limited process control, and while they can achieve limited lengths of dimensionally accurate tubing, extended runs cannot be achieved.

Another approach to tube formation is molding. However, molded tubes have physical artifacts that can be undesirable, such as parting lines and/or knit lines that form when mold components meet. Additionally, the processes used to form molded tubes can be expensive and lack flexibility. Accordingly, manufacturers of tubing can be reluctant to utilize molding processes to produce silicone tubing due to the expense and lack of flexibility of these processes and/or the undesirable appearance of visible artifacts produced by these processes. Additionally, molding cannot generally form long lengths of tubing, such as on the order of several meters and above.

Some previous attempts to provide dimensionally accurate tubing are described in the following patents and patent applications.

US Patent Application Publication No. 2001/0022411 describes catheters or other structures, such as hoses, balloons, etc., that are formed by immersing a mandrel into a number of baths. The structures can be made of silicone rubber and may have multiple layers. This application describes catheters having an overcoat layer with a preferred thickness of 0.35 mm±0.06 mm (0.0175 in.±0.0025 in.) and preferred inner layer dimensions of 0.89 mm±0.1 mm (0.035 in.±0.004 in.).

US Patent Application Publication No. 2003/0030165 describes medical catheters and tubing that are produced for intravascular procedures. The materials are preferably thermoplastics. Proximal and distal portions of the tubing have a differing stiffness and may be formed from different materials. The catheters are formed through extrusion with a melt pump that is preferably a displacement pump. Outside diameters of the tubing are to be minimized while maximizing the inside diameter. Desired dimensional tolerances for the inside diameter are about 0.0005 inches and about 0.001 inches for the outside diameter.

US Patent Application Publication No. 2003/0132552 describes tubing formed from a system that compares measured dimensions against stored target dimensions to generate feedback to adjust process variables. The melt is composed of a thermally extrudable material. Error tolerances of ±1 micron are based on the number of measurements taken by a laser gauge per second and the extrusion speed.

US Patent Application Publication No. 2006/0255497 describes thermoplastic tubing formed from an extrusion process. Tolerances for the tubing are produced by exerting pressure on the tube using rollers situated at an entry to a sizing device. A fluctuation in thickness is described as 0.1 mm for a tube having a diameter of 100 mm.

US Patent Application Publication No. 2011/0005661 describes medical tubing formed from a number of ring-shaped elements that are fused together. The process includes wrapping a stainless steel wire around a mandrel. A silicone tube may be placed around the wound coil outer diameter. Tolerances on the inner diameter can be held to 0.001 in. or less with a comparable tolerance for the outer diameter. The inner diameter may be from 0.026 in. to 0.75 in.

U.S. Pat. No. 5,759,647 describes a tubular article formed by injection molding a thermoplastic synthetic resin. The tube may have a length from several cm to more than one meter and a wall thickness ranging from less than one mm to several cm. In some cases, tubes can have a wall thickness of 2 mm with a maximum difference of wall thickness of 0.1 mm or 0.2 mm.

U.S. Pat. No. 6,508,972 describes rubber tubing formed via extrusion with a gear pump. The tubing is cut to form gaskets. A goal of the system is to produce a gasket with outer diameters and inner diameters deviating by ±0.005 in.

U.S. Pat. No. 5,948,332 describes thermoplastic material extruded to form tubing. Heating elements are provided that modify the temperature of the tubing during the extrusion process. The regulation of the temperature can exert a particular pressure on the tubing as it moves over the mandrel to produce a preferably uniform wall thickness.

U.S. Pat. No. 5,820,607 describes a multilayered tube having a hollow inner layer surrounded by a pharmacologically active substance. One or more of the layers may comprise silicone. The pharmacologically active substance may be suspended in one layer and migrate to the outer surface of the tube, the inner surface of the tube, or both. The tube may be extruded or molded and control of the overall diameter of the device is preferred. Examples of outer diameters include 3.175 mm and 1.7 mm, examples of inner diameters include 1.981 mm and 0.8 mm, and examples of layer thickness range from 0.1 mm to 3 mm.

US Patent Application Publication No. 2008/0248226 describes multi-layered tubes that are formed with a heat-shrinkable fluoropolymer liner and extruding an elastomeric cover, such as a cover having a silicone formulation, over the liner. The liners are paste extruded. A total thickness of the tube may be between 3 mils to about 50 mils and a thickness of the liner can be between 1 mil to about 20 mils The tubes are tested for length of life and tensile modulus.

Although some of the above-described documents describe a desired tolerance for certain dimensions, the prior art does not fully enable a high level of process control. Additionally, the technologies described in the foregoing prior art documents do not achieve certain dimensional tolerances over extended lengths of tubing or with respect to a specified number of tubes, and certainly not over extended lengths of tubing or tube segments therefrom.

BRIEF DESCRIPTION OF THE DRAWINGS

The present disclosure may be better understood, and its numerous features and advantages made apparent to those skilled in the art by referencing the accompanying drawings.

The use of the same reference symbols in different drawings indicates similar or identical items.

DETAILED DESCRIPTION

The following description in combination with the figures is provided to assist in understanding the teachings disclosed herein. The following discussion focuses on specific implementations and embodiments of the teachings. This focus is provided to assist in describing the teachings and should not be interpreted as a limitation on the scope or applicability of the teachings.

The disclosure generally relates to extruded silicone tubing, and in particular, to silicone tubing that has a particular dimensional accuracy. In an embodiment, a silicone tube structure can include an extruded hollow body having an inner bore. The extruded hollow body can also have an inner diameter, an outer diameter, and a length of at least approximately 20 m. In an embodiment, the extruded hollow body can have a dimensional accuracy as measured by at least one of (i) a standard deviation of the inner diameter is no greater than approximately 0.6% of an average inner diameter of the extruded hollow body over the length, and (ii) a standard deviation of a wall thickness of the extruded hollow body is no greater than approximately 1.1% over an average wall thickness of the extruded hollow body over the length. In certain instances, the silicone tube structure can be cut to form a number of silicone tubes. In other instances, the silicone tube structure can comprise a silicone tube formed from a length of silicone tubing. In a particular embodiment, a silicone tube formed from the silicone tube structure can be coupled to a pump that dispenses fluid via the silicone tube. In an illustrative embodiment, the pump may be included in a medical device that dispenses fluid to a patient via the silicone tube.

In another embodiment, a lot comprises a number of silicone tubes with each silicone tube including an extruded hollow body having an inner diameter, an outer diameter, and a length. In some instances, a standard deviation of the inner diameter of at least approximately 95% of the number of tubes in the lot is no greater than approximately 0.6% of an average inner diameter of all of the number of tubes. In other instances, a standard deviation of a wall thickness of at least approximately 95% of the number of tubes in the lot is no greater than approximately 1.1% of an average wall thickness of all of the number of tubes.

Figure 1:
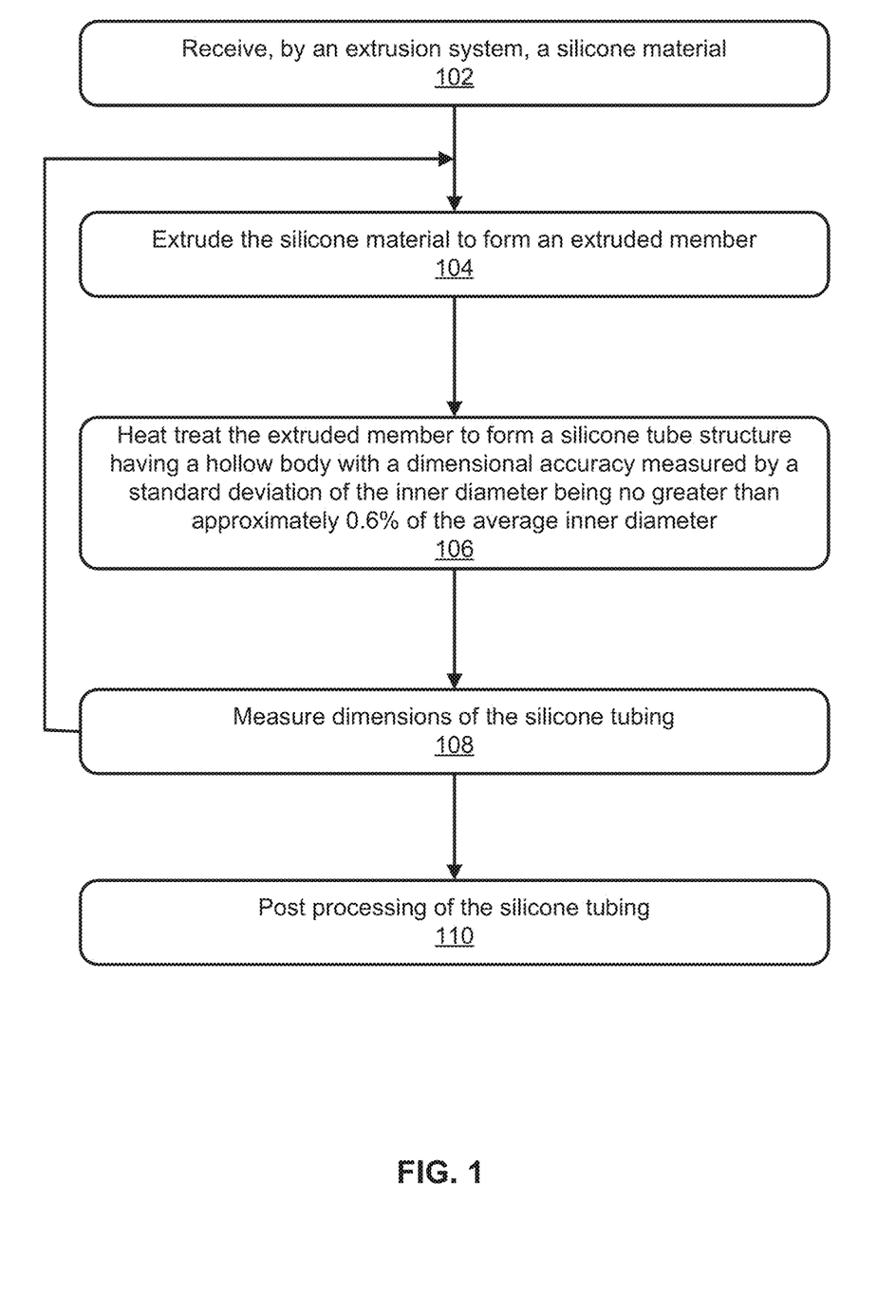
FIG. 1 is a flow diagram of a process to make silicone tubes according to an embodiment.

FIG. 1 is a flow diagram of a process 100 to make silicone tubes according to an embodiment. At 102, the process 100 includes receiving, by an extrusion system, a silicone material. An exemplary silicone material includes a silicone polymer matrix such as a polyalkylsiloxane. Any reasonable polyalkylsiloxane is envisioned. The polyalkylsiloxane can be made with a precursor such as a cyclic siloxane, a linear siloxane, a dimethylsiloxane, a diphenylsiloxane, a halosiloxane, or any combination thereof. In an example, the polyalkylsiloxane may be a gum, i.e. the polymeric matrix, used in a high consistency silicone rubber (HCR) formulation. The extrusion system can include a number of devices that can be utilized to form silicone tubing. For example, the extrusion system can include one or more extrusion devices, one or more heat treatment devices, one or more measurement devices, one or more post-processing devices, or any combination thereof.

At 104, the process 100 includes extruding the silicone material to form an extruded member. In an embodiment, the extruded member can be formed by providing the silicone material to a die and mandrel. In some instances, the silicone material can be heated and mixed before being provided to the die and mandrel.

At 106, the process 100 includes heat treating the extruded member to form silicone tubing having a hollow body with an inner bore and a particular dimensional accuracy. In an embodiment, the heat treatment of the extruded member can include subjecting the extruded member to one or more curing operations.

At 108, the process 100 includes measuring dimensions of the silicone tubing. In an embodiment, the dimensions of the silicone tubing can be measured using a laser sensor, an X-ray device, or both. Additionally, the dimensions of the silicone tubing can be measured along a number of points of the body of the tubing. In certain instances, the dimensions of the silicone tubing can be measured at a particular interval, such as at least every 0.5 seconds, at least every 1.5 seconds, at least every 5 seconds, at least every 10 seconds, or at least every 20 seconds. In a particular embodiment, the outer diameter of the hollow body of the silicone tubing can be measured. In another embodiment, the wall thickness of the silicone tubing can be measured. Further, the inner diameter of the silicone tubing can be measured.

In some cases, the measurements of the dimensions of the silicone tubing can be provided as feedback information to a control system. Based on the feedback information, the control system can adjust parameters of the extrusion system to maintain the dimensional accuracy of the silicone tubing.

At 110, the silicone tubing can undergo one or more post processing operations. To illustrate, the silicone tubing can comprise a silicone tube structure that is cut into a number of silicone tubes having a specified length. In an embodiment, at least 95% of the silicone tubes can have a specified dimensional accuracy. In some instances, the dimensional accuracy can be measured by a standard deviation of an inner diameter of the silicone tube structure being no greater than approximately 0.6% of an average inner diameter of the silicone tube structure over a length of the silicone tube structure. In certain embodiments, the standard deviation of the inner diameter may be no greater than approximately 0.5% of the average inner diameter, no greater than approximately 0.4% of the average inner diameter, no greater than approximately 0.2% of the average inner diameter, or no greater than approximately 0.08% of the average inner diameter.

Additionally, the dimensional accuracy can be measured by a standard deviation of a wall thickness of the silicone tube structure being no greater than approximately 1.1% of an average wall thickness of the tube over the length of the tube. In particular embodiments, the standard deviation of the wall thickness may be no greater than approximately 0.8% of the average wall thickness, no greater than approximately 0.6% of the average wall thickness, no greater than approximately 0.4% of the average wall thickness, no greater than approximately 0.2% of the average wall thickness, or no greater than approximately 0.08% of the average wall thickness.

Figure 2:
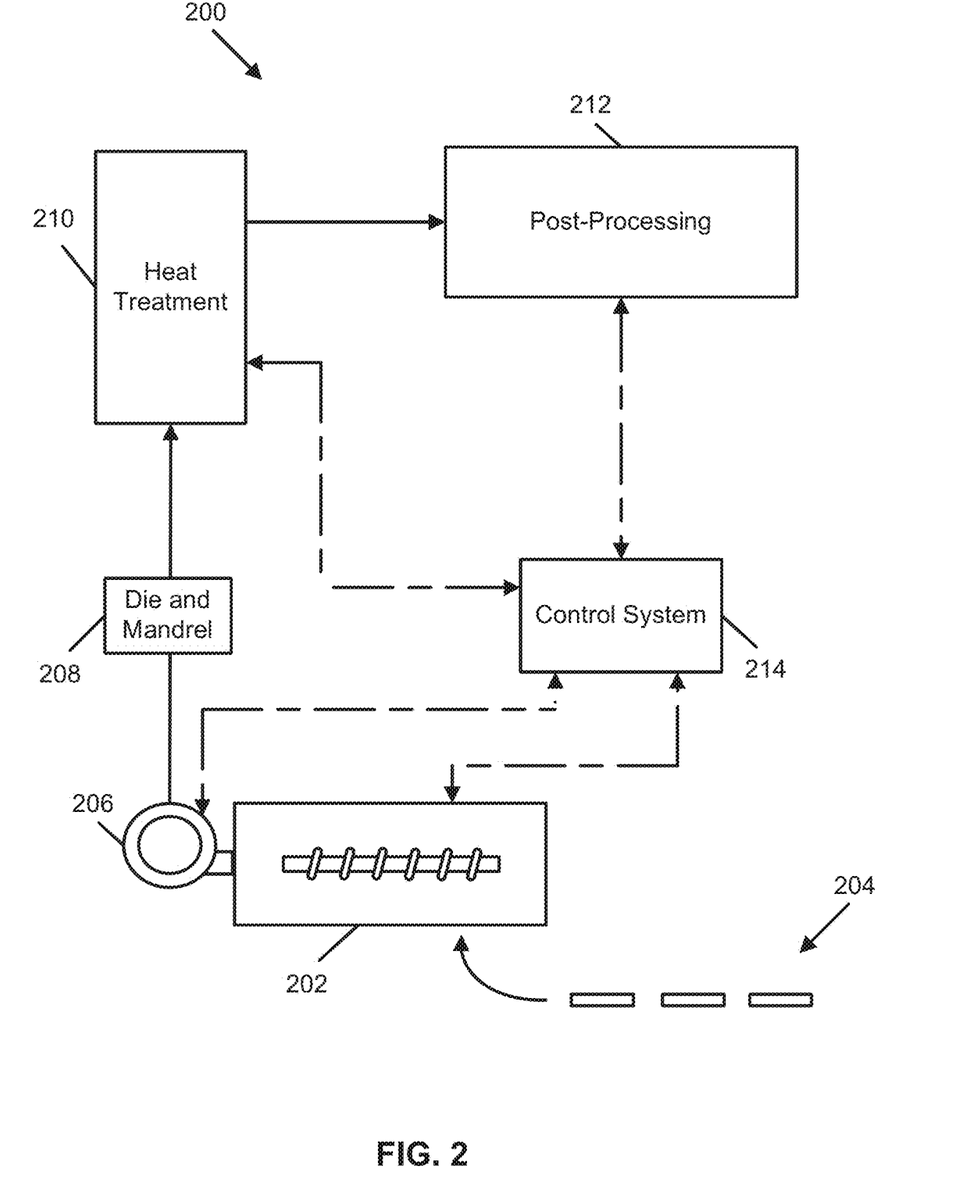
FIG. 2 is a diagram of an embodiment of an extrusion system to make silicone tubes.

FIG. 2 is a diagram of an embodiment of an extrusion system 200 to make silicone tubes. In a particular embodiment, the extrusion system 200 can implement the process 100 to form silicone tube structures having a specified dimensional accuracy.

The extrusion system 200 can include an extruder 202, such as a single screw extruder. The extruder 202 can melt and/or mix feed material 204. The feed material 204 can be a silicone material that can be formed into tubing. In an embodiment, the feed material 204 can be provided to the single screw extruder 202 in the form of a solid, such as pellets, strips, powders, and the like. In addition, the feed material 204 can comprise a mixture of a number of components, such as a number of siloxane polymers, to be used to form silicone tubing.

In certain situations, particular additives can be fed to the single screw extruder 202 as a portion of the feed material 204. In an embodiment, the additives can include one or more fillers. In some instances, the one or more fillers can comprise $SiO_2$. Additionally, the one or more fillers can comprise no greater than approximately 80% by weight of the feed material 204. In some embodiments, the one or more filler materials can comprise no greater than approximately 55% by weight of the feed material 204, no greater than approximately 35% by weight of the feed material 204, no greater than approximately 28% by weight of the feed material 204, no greater than approximately 21% by weight of the feed material, no greater than approximately 14% by weight of the feed material, or no greater than approximately 6% by weight of the feed material 204. Further, the one or more fillers can comprise at least approximately 0.5% by weight of the feed material 204, at least approximately 4% by weight of the feed material 204, at least approximately 9% by weight of the feed material 204, or at least approximately 18% by weight of the feed material. It will be appreciated that the one or more fillers can comprise an amount of the feed material 204 within a range between any of the values noted above.

In another embodiment, the feed material 204 can include a cure package, such as a platinum cure package or a peroxide cure package. In a particular embodiment, the cure package can include a catalyst, an initiator, an inhibitor, a vinyl polymer, a hydride, one or more carrier materials, or a combination thereof. Typically, in its uncured state, the feed material 204 has a plasticity of about 1.0 mm to about 6.0 mm, when tested for three minutes at 70° F. using a Precision Scientific Plasticity tester per ASTM D926-80 Procedure A. In an embodiment, the materials of the cure package can comprise at least approximately 0.1% by weight of the feed material 204. In another embodiment, the materials of the cure package can comprise no greater than approximately 99.9% by weight of the feed material 204. In certain embodiments, the materials of the cure package can comprise no greater than approximately 55% by weight of the feed material 204, no greater than approximately 38% by weight of the feed material 204, no greater than approximately 26% by weight of the feed material 204, no greater than approximately 18% by weight of the feed material 204, or no greater than approximately 11% by weight of the feed material 204. Additionally, the materials of the cure package can comprise at least approximately 0.25% by weight of the feed material 204, at least approximately 1.5% by weight of the feed material 204, at least approximately 7% by weight of the feed material 204, at least approximately 14% by weight of the feed material 204, at least approximately 22% by weight of the feed material 204, or at least approximately 44% by weight of the feed material 204. It will be appreciated that the cure package can comprise an amount of the feed material 204 within a range between any of the values noted above.

The extruder 202 is coupled to a gear pump 206. In an embodiment, the gears of the gear pump 206 can have a double helix design. The gear pump 206 can operate with suctions pressures in a range between 500 to 2000 psi, such as 700 psi to 1700 psi. In some embodiments, the suction pressure of the gear pump 206 may be no greater than approximately 1550 psi, no greater than approximately 1380 psi, or no greater than approximately 1090 psi. Additionally, the gear pump 206 can operate with head pressures in a range between 1000 psi and 4000 psi, such as 1500 to 4000 psi. In an embodiment, the head pressures of the gear pump 206 may be no greater than approximately 3400 psi, no greater than approximately 2700 psi, or no greater than approximately 2500 psi.

Particular attention is drawn to use of a gear pump in combination with the extruder. Typical prior process flows rely on use of an extruder. However, it was found through experimentation that the combination of an extruder with a gear pump worked well according to certain embodiments.

The extrusion system 200 can operate at a speed of at least approximately 5 m/min, at least approximately 22 m/min, at least approximately 30 m/min, at least approximately 40 m/min, or at least approximately 50 m/min. In addition, the speed of the extrusion system 200 can be limited, such as no greater than approximately 200 m/min, no greater than approximately 150 m/min, or no greater than approximately 90 m/min It will be appreciated that the speed of the extrusion system 200 can be within a range between any of the minimum and maximum values noted above.

The extrusion system 202 can also include a die and mandrel 208. Although the die and mandrel 208 are shown separate from the extruder 202, in some embodiments, the die and mandrel 208 can be a component of the extruder 202. In a particular embodiment, a ratio of the land length of the die to the wall thickness of a body of the silicone tubing formed via the extrusion system 200 can be no greater than approximately 6:1, no greater than approximately 5:1, or no greater than approximately 4:1.

According to certain embodiments, extrusion was operated at a draw down percentage, DD %. DD % relates to the % by which the outer diameter of the tube differs from an outer diameter of the die void. This parameter is affected by a number of parameters, including die flow and line speed. Prior processes have focused on fairly large DD %, such as on the order of 20-30%, while others have used minimal DD %, such as 0-2%. In contrast, embodiments herein can use a DD % on the order of 3 to 15%, 5 to 13%, such as 5 to 10%, or 7 to 10%.

After forming an extruded member having an inner bore with the die and mandrel 208, the extruded member can be subjected to heat treatment 210 to form silicone tubing having an extruded hollow body with an inner bore. The heat treatment 210 can include one or more curing processes, one or more drying processes, or a combination thereof. Curing provides a silicone tubing having a Shore A durometer of about 20 to about 90. For example, the extrusion system 200 can include one or more ovens (e.g. infrared (IR) ovens, air ovens), one or more baths (e.g. salt water baths), or a combination thereof, to cure the extruded member. The one or more IR ovens can operate at a particular peak wavelength. In certain instances, the peak wavelength of a first IR oven can be different from the peak wavelength of a second IR oven. In an embodiment, the extruded member can be subjected to the heat treatment 210 for a specified period of time. In a particular embodiment, the silicone tubing can be subjected to curing in a first IR oven for a first period of time and then subject to curing in a second IR oven for a second period of time that is different from the first period of time. In one particular embodiment, use is made of a short wavelength IR oven. By short wavelength, it is meant that the peak wavelength is below 4 microns, typically below 3 microns, such as within a range of approximately 0.6 to 2.0 microns, such as 0.8 to 1.8 microns. Generally medium and longer wavelength IR ovens are characterized by a peak wavelength on the order of 4 to 8 microns, or even higher.

Without being wished to be bound by any particular theory, it is believed that use of a short wavelength IR oven may be particularly useful for certain embodiments. It is theorized that the short wavelength IR oven may function to quickly cure material existing at outer surfaces to assist in preventing post-extrusion distortion.

The cured silicone tubing can undergo post processing 212. In an embodiment, the post processing 212 can include cutting the silicone tubing into a number of silicone tubes of particular lengths. In some instances, a number of the silicone tubes can be grouped to form a lot of silicone tubes. In another embodiment, the post processing 212 can include wrapping the silicone tubing into a coil of tubing.

The extrusion system 200 can also include a control system 214 that includes one or more computing devices. The control system 214 can provide signals to one or more of the components of the extrusion system 200 to specify operating conditions for the components. For example, the control system 214 can adjust a speed of the extrusion system 200 based on the measurements of the dimensions of the silicone tube. In another example, the control system 214 can adjust the temperature of one or more heat treatment devices of the extrusion system 200 based on the measurements of the dimensions of the silicone tube. Further, the control system 200 can adjust the suction pressure of the gear pump 206 based on the measurements of the dimensions of the silicone tube.

In certain instances, the signals provided by the control system 214 can be based, at least partly, on feedback information provided by one or more sensors of the extrusion system 200. In some embodiments, the one or more sensors can be part of a component of the extrusion system 200, such as a pressure sensor of the pump 206, a temperature sensor of components providing the heat treatment 210, or a combination thereof. In other embodiments, the one or more sensors, such as a laser gage or X-ray device, can be disposed between components of the extrusion system 200 to measure dimensions of the silicone tubing between the components providing the heat treatment 210 and the components performing the post processing 212. Additionally, one or more sensors can be disposed between the die and mandrel 208 and the components providing the heat treatment 210 to measure dimensions of the silicone tubing. In certain implementations, the dimensions measured by the sensors can represent dimensions of non-postcured silicone tubing. Non-postcured silicone tubing can refer to silicone tubing that has not been subjected to an additional curing operation after undergoing the heat treatment 210.

In the illustrative embodiment shown in FIG. 2, the extrusion system 200 is organized such that one or more components of the extrusion system 200 are arranged in a vertical configuration. For example, the extruder 202, the die and mandrel 208, and the components of the heat treatment 210 are arranged to vertically extrude silicone tubing. In a particular embodiment, the silicone tubing can be formed by extruding the silicone material 204 in an upward direction.

The extrusion system 200 can operate to form a particular number of silicone tubes or a particular length of silicone tubing having a specified dimensional accuracy that is not achieved by conventional silicone tube manufacturing processes. In particular, through extended experimentation, a particular combinations and arrangements of the components of the extrusion system and the operating parameters have been found to form dimensionally accurate tubing; tubing with dimensional control that conventional extrusion systems and process flows are not able to achieve. A number of features can be used alone or in combination including subcombinations: (i) coupling the gear pump to the extruder, (ii) a combination of suction pressure and head pressure within the ranges described, (iii) arranging the extrusion system such that the tubing is extruded in a vertically upward direction, (iv) use of a short wavelength IR oven, and/or (v) use of particular DD % values. It is noted that prior processes typically do not rely on the combination of an extruder and gear pump; consequently the only pressure of concern in such prior processes is head (output) pressure as there is no suction pressure to be set. It is emphasized that the arrangement of the components of the extrusion system and the operating parameters for the components are empirical in nature, the result of experimentation and extended development efforts.

Figure 3:
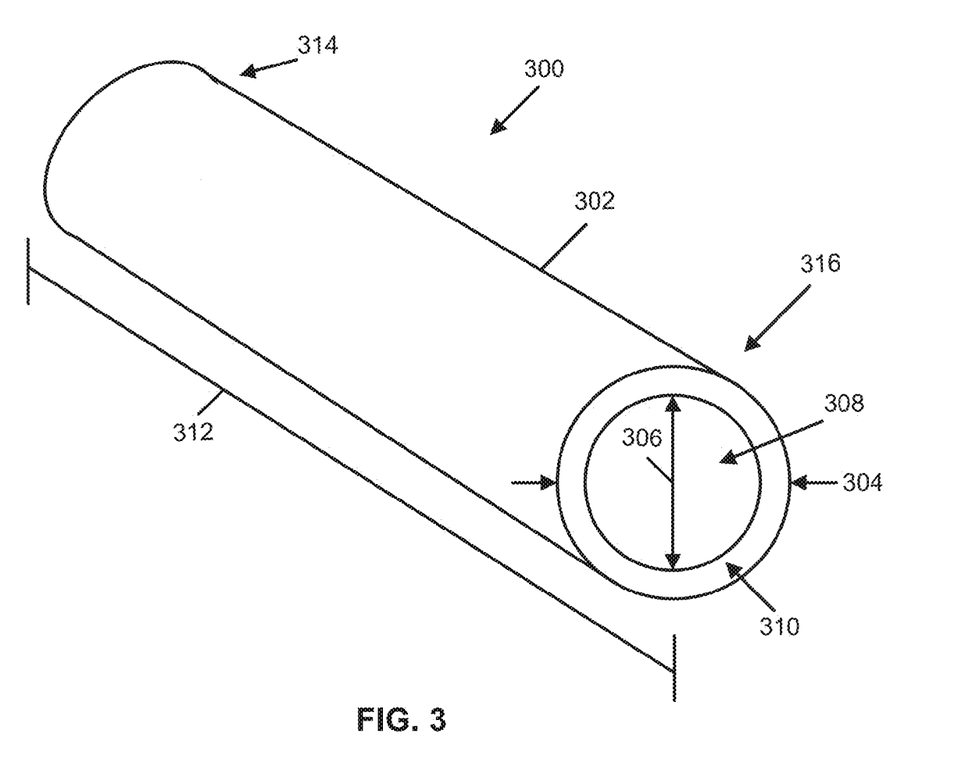
FIG. 3 is a view of an extruded silicone tube structure according to an embodiment.

FIG. 3 is a view of an extruded silicone tube structure 300 according to an embodiment. In a particular embodiment, the silicone tube structure 300 can be formed according to the process 100 described previously with respect to FIG. 1 and by the extrusion system 200 described previously with respect to FIG. 2. Thus, the silicone tube structure 300 has the specified dimensional accuracy produced by utilizing the extrusion system 200 to implement the process 100.

The silicone tube structure 300 can include a body 302 having an outer diameter 304 and an inner diameter 306. The inner diameter 306 can form a hollow bore 308 of the body 302. In addition, the body 302 can include a wall thickness 310 that is measured by the difference between the outer diameter 304 and the inner diameter 306. Further, the body 302 can have a length 312.

In a particular embodiment, the outer diameter 304 can be at least approximately 4 mm, at least approximately 8 mm, or at least approximately 11 mm Additionally, the outer diameter 304 can be no greater than approximately 9 mm, no greater than approximately 12 mm, or no greater than approximately 15 mm. It will be appreciated that the outer diameter 304 can be within a range between any of the minimum and maximum values noted above.

In another embodiment, the inner diameter 306 of the body 302 can be at least approximately 2 mm, at least approximately 4 mm, or at least approximately 6 mm Further, the inner diameter 306 can be no greater than approximately 5 mm, no greater than approximately 7 mm, or no greater than approximately 9 mm It will be appreciated that the inner diameter 306 can be within a range between any of the minimum and maximum values noted above.

In a further embodiment, the length 312 of the body 302 can be at least approximately 22 m, at least approximately 26 m, at least approximately 34 m, or at least approximately 45 m. In another embodiment, the length 312 can be at least approximately 30 m, at least approximately 50 m, at least approximately 100 m, or at least approximately 125 m. The length 312 is generally limited by pragmatic concerns, such as storing and transporting long lengths, or by customer demand for limited production runs, such as 20 m or 100 m. In another embodiment, the length 312 can be at least approximately 30 m, at least approximately 50 m, at least approximately 100 m, or at least approximately 125 m.

Although the cross-section of the inner bore 306 perpendicular to an axial direction of the body 302 in the illustrative embodiment shown in FIG. 3 has a circular shape, the cross-section of the inner bore 306 perpendicular to the axial direction of the body 302 can have a square shape, a triangular shape, or a rectangular shape. It should also be noted that the silicone tube structure 300 is free from any of the visual defects found on tubes formed by a molding process. For example, the silicone tube structure 300 does not include any parting lines. Additionally, knit lines are absent from one or more ends of the body 302, such as a distal end 314, a proximal end 316, or both.

Furthermore, although the silicone tube structure 300 of the illustrative embodiment shown in FIG. 3 has a single lumen comprising the hollow bore 308, in other embodiments, the silicone tube structure 300 can have a plurality of lumen. In addition, each of the respective lumen of the plurality of lumen can have an inner diameter. In an embodiment, the inner diameter of at least one respective lumen of the plurality of lumen has a standard deviation that is no greater than approximately 0.8% of an average inner diameter of the at least one respective lumen over the length 312.

Figure 4:
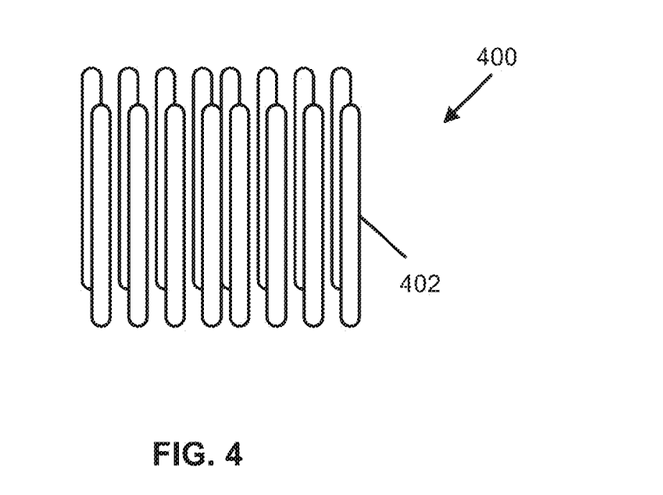
FIG. 4 is a view of a lot of extruded silicone tubes according to an embodiment.

FIG. 4 is a view of a lot 400 comprising a number of extruded silicone tubes 402 according to an embodiment. It will be appreciated that although the lot 400 illustrated in FIG. 4 includes a particular number of tubes 402, the lot 400 can include any number of tubes 402. For example, in one embodiment, the number of extruded silicone tubes 402 in the lot 400 can be at least approximately 10, at least approximately 45, at least approximately 110, or at least approximately 170. In another embodiment, the number of extruded silicone tubes 402 in the lot 400 may be no greater than approximately 750, no greater than approximately 500, no greater than approximately 380, no greater than approximately 275, no greater than approximately 210, or no greater than approximately 155. It will be appreciated that the number of extruded silicone tubes 402 in the lot 400 can be within a range between any of the minimum and maximum values noted above.

Additionally, the length of the silicone tubes 402 of the lot 400 can be at least approximately 8 cm, at least approximately 16 cm, or at least approximately 24 cm. The length of the silicone tubes 402 of the lot 400 may be no greater than approximately 40 cm, no greater than approximately 30 cm, or no greater than approximately 20 cm. It will be appreciated that the length of the silicone tubes 402 of the lot 400 can be within a range between any of the minimum and maximum values noted above.

In an embodiment, each of the silicone tubes 402 of the lot 400 can be formed from a silicone tube structure that is manufactured according to the process 100 described previously with respect to FIG. 1 and by the extrusion system 200 described previously with respect to FIG. 2. Thus, in some instances, each of the individual tubes 402 can have the specified dimensional accuracy produced by utilizing the extrusion system 200 to implement the process 100. In a particular embodiment, the dimensional accuracy of the extruded silicone tubes 402 of the lot 400 can be measured by the standard deviation of the inner diameter of at least approximately 97% of the number of silicone tubes 402 being no greater than approximately 0.6% of the average inner diameter of all of the number of tubes 402, the standard deviation of the inner diameter of at least approximately 99% of the number of tubes 402 being no greater than approximately 0.6% of the average inner diameter of all of the number of tubes 402, the standard deviation of the inner diameter of at least approximately 99.5% of the number of tubes 402 being no greater than approximately 0.6% of the average inner diameter of all of the number of tubes 402, the standard deviation of the inner diameter of at least approximately 99.9% of the number of tubes 402 being no greater than approximately 0.6% of the average inner diameter of all of the number of tubes 402, or the standard deviation of the inner diameter of at least approximately 99.99% of the number of tubes 402 being no greater than approximately 0.6% of the average inner diameter of all of the number of tubes 402. In another embodiment, the dimensional accuracy of the extruded silicone tubes 402 of the lot 400 can be measured by the standard deviation of the wall thickness of at least approximately 97% of the number of tubes 402 being no greater than approximately 1.1% of the average wall thickness of all of the number of tubes 402, the standard deviation of the wall thickness of at least approximately 99% of the number of tubes 402 being no greater than approximately 1.1% of the average wall thickness of all of the number of tubes 402, the standard deviation of the wall thickness of at least approximately 99.5% of the number of tubes 402 being no greater than approximately 1.1% of the average wall thickness of all of the number of tubes 402, the standard deviation of the wall thickness of at least approximately 99.9% of the number of tubes 402 being no greater than approximately 1.1% of the average wall thickness of all of the number of tubes 402, or the standard deviation of the wall thickness of at least approximately 99.99% of the number of tubes 402 being no greater than approximately 1.1% of the average wall thickness of all of the number of tubes 402.

The foregoing standard deviation percentages are particularly applicable to a range of tube inner diameters, notably ID ranges from about 2.0 to 25.0 mm, such as 2.0 to 20.0 mm, 2.5 to 20 mm, and 3.0 to 20 mm It is noted that, in general, low standard deviation percentages are quite difficult to achieve for larger diameter tubing, such as those at 2.5 mm and above, such as 3.0 mm or above. Consequently, embodiments of the invention have particular relevance for larger diameter tubing.

Figure 5:
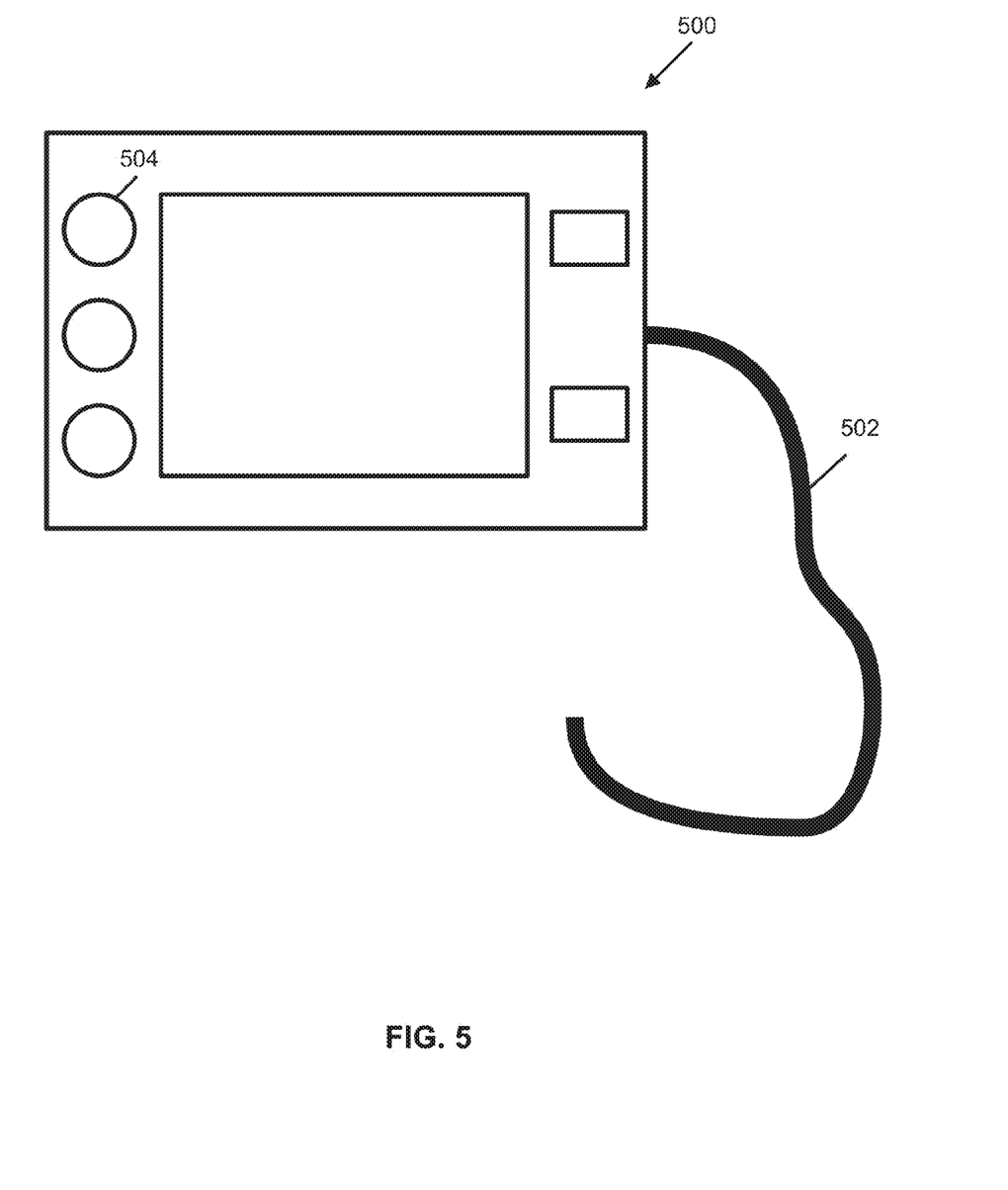
FIG. 5 is a diagram of a medical device coupled to an extruded silicone tube according to an embodiment.

FIG. 5 is a diagram of a medical device 500 coupled to an extruded silicone tube 502 according to an embodiment. The silicone tube 502 can be formed from the silicone tube structure 300 of FIG. 3 or the silicone tube 502 can be one of the silicone tubes of the lot 400 of FIG. 4. In an embodiment, the medical device 500 can include a pump to dispense fluid to a patient via the silicone tube 502. In an embodiment, the medical device 500 can include a peristaltic pump, an infusion pump, an affinity pump, an enteral pump, or a combination thereof.

The silicone tube 502 can contribute to providing a specified amount of fluid to a patient. For example, one or more controls, such as the control 504, can be set to provide a specified flow rate of fluid into a patient. Due to the dimensional accuracy of the silicone tube 502, an amount of fluid can be dispensed to a patient that is within a particular tolerance in relation to the amount specified via the control 504.

In an embodiment, the flow rate of the fluid can be at least approximately 0.1 mL/hr., at least approximately 100 mL/hr., at least approximately 400 mL/hr., or at least approximately 700 mL/hr. In another embodiment, the flow rate of the fluid may be no greater than approximately 1500 mL/hr., no greater than approximately 1200 mL/hr., no greater than approximately 900 mL/hr., or no greater than approximately 500 mL/hr. It will be appreciated that the flow rate can be within a range between any of the above minimum and maximum values noted above.

Embodiments may be in accordance with any one or more of the items as listed below. A first set of items are as follows:

Item 1. A silicone tube structure comprising: an extruded hollow body having an inner bore, the extruded hollow body having an inner diameter, an outer diameter, and a length of at least approximately 20 m; wherein a standard deviation of the inner diameter is no greater than approximately 0.6% of an average inner diameter of the extruded hollow body over the length.

Item 2. An apparatus comprising: a silicone tube formed from a silicone tube structure comprising an extruded hollow body having an inner bore, the extruded hollow body having an inner diameter, an outer diameter, and a length of at least approximately 20 m, wherein a standard deviation of the inner diameter is no greater than approximately 0.6% of an average inner diameter of the extruded hollow body over the length; and a pump to dispense fluid via the silicone tube.

Item 3. The apparatus as recited in item 2, wherein the silicone tube and the pump comprise a medical device to provide the fluid to a patient.

Item 4. A method comprising: providing a medical device comprising a pump and a silicone tube formed from a silicone tube structure, the silicone tube structure comprising an extruded hollow body having an inner bore, the extruded hollow body having an inner diameter, an outer diameter, and a length of at least approximately 20 m, wherein a standard deviation of the inner diameter is no greater than approximately 0.6% of an average inner diameter of the extruded hollow body over the length; and dispensing fluid to a patient with the medical device.

Item 5. The apparatus or method as recited in any one of items 2 to 4, wherein the pump is a peristaltic pump.

Item 6. The apparatus or method as recited in any one of items 2 to 5, wherein the pump is an infusion pump, an affinity pump, or an enteral pump.

Item 7. The apparatus or method as recited in any one of items 2 to 6, wherein a flow rate of the fluid is at least approximately 0.1 mL/hr., at least approximately 100 mL/hr., at least approximately 400 mL/hr., or at least approximately 700 mL/hr.

Item 8. The apparatus or method as recited in any one of items 2 to 6, wherein a flow rate of the fluid is no greater than approximately 1500 mL/hr., no greater than approximately 1200 mL/hr., no greater than approximately 900 mL/hr., or no greater than approximately 500 mL/hr.

Item 9. A method comprising: receiving, by an extrusion system, a silicone material; and forming, by the extrusion system, a silicone tube structure from the silicone material, the silicone tube structure comprising a body having an inner bore, the body having an inner diameter, an outer diameter, and a length of at least approximately 20 m, wherein a standard deviation of the inner diameter is no greater than approximately 0.6% of an average inner diameter of the extruded hollow body over the length.

Item 10. The method as recited in item 9, wherein forming the silicone tube structure from the silicone material includes: extruding the silicone material to form an extruded member; and curing the extruded member to form the silicone tube.

Item 11. The method as recited in items 9 or 10, wherein one or more components of the extrusion system are arranged in a vertical configuration.

Item 12. The method as recited in item 11, wherein the silicone material is extruded vertically in an upward direction.

Item 13. The method as recited in any one of items 11 to 12, wherein the extrusion system includes at least one curing apparatus.

Item 14. The method as recited in item 13, wherein the at least one curing apparatus includes one or more infrared (IR) ovens.

Item 15. The method as recited in item 10, further comprising providing the extruded member to a first IR oven for a specified period of time and providing the extruded member to a second IR oven for an additional specified period of time.

Item 16. The method as recited in item 15, wherein the extruded member is provided to the second IR oven after the extruded member is provided to the first IR oven.

Item 17. The method as recited in item 10, wherein the extrusion system includes a gear pump.

Item 18. The method as recited in item 17, wherein the gear pump operates with a particular range of suction pressures based at least partly on a range of head pressures of the gear pump.

Item 19. The method as recited in item 18, wherein the range of head pressures of the gear pump is based at least partly on a composition of the silicone material, the length of the body, a viscosity of the silicone material, a speed of the extrusion system, or any combination thereof.

Item 20. The method as recited in item 17, wherein gears of the gear pump have a double helix design.

Item 21. The method as recited in any one of items 10 to 20, wherein a speed of the extrusion system is at least approximately 2 m/min, at least approximately 22 m/min, at least approximately 40 m/min, at least approximately 80 m/min, or at least approximately 110 m/min.

Item 22. The method as recited in any one of items 10 to 20, wherein a speed of the extrusion system is no greater than approximately 200 m/min, no greater than approximately 150 m/min, no greater than approximately 90 m/min, no greater than approximately 60 m/min, no greater than approximately 30 m/min, or no greater than approximately 12 m/min.

Item 23. The method as recited in any one of items 10 to 22, wherein the extrusion system includes an extruder having a die and a mandrel.

Item 24. The method as recited in item 23, wherein a ratio of a land length of the die to the wall thickness of the body is no greater than approximately 6:1, no greater than approximately 5:1, or no greater than approximately 4:1.

Item 25. The method as recited in items 23 or 24, wherein the extruder is a single screw extruder.

Item 26. The method as recited in any one of items 10 to 16, further comprising determining the outer diameter at a particular point of the body.

Item 27. The method as recited in item 26, wherein the outer diameter at the particular point of the body is determined using a laser sensor or an X-ray sensor.

Item 28. The method as recited in items 26 or 27, wherein the outer diameter at the particular point of the body is determined at a particular interval.

Item 29. The method as recited in item 28, wherein the particular interval is at least approximately every 0.5 seconds, at least approximately every 1.5 seconds, at least approximately every 5 seconds, at least approximately every 10 seconds, or at least approximately every 20 seconds.

Item 30. The method as recited in any one of items 26 to 29, further comprising adjusting a suction pressure of a gear pump of the extruder system based on the outer diameter at the particular point of the body, adjusting a speed of the extruder system based on the outer diameter at the particular point of the body, adjusting a temperature of one or more IR ovens of the extruder system based on the outer diameter at the particular point of the body, or any combination thereof.

Item 31. The method as recited in any one of items 9 to 30, further comprising measuring one or more dimensions of the silicone tube structure before postcuring of the silicone tube structure.

Item 32. The silicone tube structure, apparatus, or method as recited in any one of the preceding items, wherein the standard deviation of the inner diameter is no greater than approximately 0.5% of the average inner diameter of the extruded hollow body over the length, no greater than approximately 0.4% of the average inner diameter of the extruded hollow body over the length, no greater than approximately 0.2% of the average inner diameter of the extruded hollow body over the length, or no greater than approximately 0.08% of the average inner diameter of the extruded hollow body over the length.

Item 33. The silicone tube structure, apparatus, or method as recited in any one of the preceding items, wherein a standard deviation of a wall thickness of the extruded hollow body is no greater than approximately 1.1% of an average wall thickness of the extruded hollow body over the length, no greater than approximately 0.8% of the average wall thickness of the extruded hollow body over the length, no greater than approximately 0.6% of the average wall thickness of the extruded hollow body over the length, no greater than approximately 0.4% of the average wall thickness of the extruded hollow body over the length, no greater than approximately 0.2% of the average wall thickness of the extruded hollow body over the length, or no greater than approximately 0.08% of the average wall thickness of the extruded hollow body over the length.

Item 34. The silicone tube structure, apparatus, or method as recited in any one of the preceding items, wherein a cross-section of the inner bore perpendicular to an axial direction of the body has a circular shape, a square shape, a triangular shape, or a rectangular shape.

Item 35. The silicone tube structure, apparatus, or method as recited in any one of the preceding items, wherein the length of the body is at least approximately 22 m, at least approximately 26 m, at least approximately 34 m, or at least approximately 45 m.

Item 36. The silicone tube structure, apparatus, or method as recited in any one of the preceding items, wherein the length of the body is no greater than approximately 100 m, no greater than approximately 82 m, no greater than approximately 68 m, or no greater than approximately 53 m.

Item 37. The silicon tube structure, apparatus, or method as recited in any one of the preceding items, wherein the inner diameter of the body is at least approximately 2 mm, at least approximately 4 mm, or at least approximately 6 mm.

Item 38. The silicone tube structure, apparatus, or method as recited in any one of the preceding items, wherein the inner diameter of the body is no greater than approximately 5 mm, no greater than approximately 7 mm, or no greater than approximately 9 mm.

Item 39. The silicon tube structure, apparatus, or method as recited in any one of the preceding items, wherein the outer diameter of the body is at least approximately 4 mm, at least approximately 8 mm, or at least approximately 11 mm.

Item 40. The silicone tube structure, apparatus, or method as recited in any one of the preceding, items wherein the outer diameter of the body is no greater than approximately 9 mm, no greater than approximately 12 mm, or no greater than approximately 15 mm.

Item 41. The silicone tube structure, apparatus, or method as recited in any one of the preceding items, wherein the silicone tube comprises a polymer including a cyclic siloxane, a linear siloxane, a dimethylsiloxane, a diethylsiloxane, a diphenylsiloxane, a halosiloxane, or any combination thereof.

Item 42. The silicone tube structure, apparatus, or method as recited in any one of the preceding items, wherein a knit line is absent from a distal end of the body of the silicone tube and a proximal end of the body of the silicone tube.

Item 43. The silicone tube structure, apparatus or method as recited in any one of the preceding items, wherein the silicone tube structure is cut into a number of silicone tubes.

Item 44. The silicone tube structure, apparatus, or method as recited in item 43, wherein the number of silicone tubes comprise at least a portion of a lot of tubes.

Item 45. The silicone tube structure, apparatus, or method as recited in any one of the preceding items, wherein the silicone tube structure comprises a plurality of lumen, each lumen of the plurality of lumen has a respective inner diameter, and the respective inner diameter of at least one lumen of the plurality of lumen has a standard deviation that is no greater than approximately 0.8% of an average inner diameter of the at least one lumen over the length.

Item 46. A lot comprising a number of silicone tubes, each silicone tube including an extruded hollow body having an inner diameter, an outer diameter, and a length, wherein a standard deviation of the inner diameter of at least approximately 95% of the number of tubes is no greater than approximately 0.6% of an average inner diameter of all of the number of tubes.

Item 47. The lot of item 46, wherein the number of silicone tubes is at least approximately 10, at least approximately 45, at least approximately 110, or at least approximately 170.

Item 48. The lot of item 46 or 47, wherein the number of silicone tubes is no greater than approximately 750, no greater than approximately 500, no greater than approximately 380, no greater than approximately 275, no greater than approximately 210, or no greater than approximately 155.

Item 49. The lot of any one of items 46 to 48, wherein the length of each silicone tube is no greater than approximately 40 cm, no greater than approximately 30 cm, or no greater than approximately 20 cm.

Item 50. The lot of any one of items 46 to 49, wherein the length of each silicone tube is at least approximately 8 cm, at least approximately 16 cm, or at least approximately 24 cm.

Item 51. The lot of any one of items 46 to 50, wherein the standard deviation of the inner diameter of at least approximately 97% of the number of tubes is no greater than approximately 0.6% of the average inner diameter of all of the number of tubes, the standard deviation of the inner diameter of at least approximately 99% of the number of tubes is no greater than approximately 0.6% of the average inner diameter of all of the number of tubes, the standard deviation of the inner diameter of at least approximately 99.5% of the number of tubes is no greater than approximately 0.6% of the average inner diameter of all of the number of tubes, the standard deviation of the inner diameter of at least approximately 99.9% of the number of tubes is no greater than approximately 0.6% of the average inner diameter of all of the number of tubes, or the standard deviation of the inner diameter of at least approximately 99.99% of the number of tubes is no greater than approximately 0.8% of the average inner diameter of all of the number of tubes.

Item 52. The lot of any one of items 46 to 51, wherein a standard deviation of a wall thickness of at least approximately 95% of the number of tubes is no greater than approximately 1.1% of an average wall thickness of all of the number of tubes, the standard deviation of the wall thickness of at least approximately 97% of the number of tubes is no greater than approximately 1.1% of the average wall thickness of all of the number of tubes, the standard deviation of the wall thickness of at least approximately 99% of the number of tubes is no greater than approximately 1.1% of the average wall thickness of all of the number of tubes, the standard deviation of the wall thickness of at least approximately 99.5% of the number of tubes is no greater than approximately 1.1% of the average wall thickness of all of the number of tubes, the standard deviation of the wall thickness of at least approximately 99.9% of the number of tubes is no greater than approximately 1.1% of the average wall thickness of all of the number of tubes, or the standard deviation of the wall thickness of at least approximately 99.99% of the number of tubes is no greater than approximately 1.1% of the average wall thickness of all of the number of tubes.

Item 53. The lot of any one of items 46 to 52, wherein one or more silicone tubes of the number of silicone tubes are formed from the silicone tube structure of any one of items 1 to 45.

Item 54. The silicone tube structure, method, or apparatus according to any of the preceding items wherein the tube or tubes have a nominal diameter of at least about 2.0 mm, such as at least about 2.5 mm, such as at least about 3.0 mm, or about 2.0 to 25.0 mm, such as 2.0 to 20.0 mm, 2.5 to 20 mm, and 3.0 to 20 mm.

Another set of items are described below:

Item 1. A silicone tube structure comprising:
an extruded hollow body having an inner bore, the extruded hollow body having an inner diameter, an outer diameter, and a length of at least approximately 20 m;
wherein a standard deviation of the inner diameter is no greater than approximately 0.6% of an average inner diameter of the extruded hollow body over the length.

Item 2. A method comprising:
receiving, by an extrusion system, a silicone material; and
forming, by the extrusion system, a silicone tube structure from the silicone material, the silicone tube structure comprising an extruded hollow body having an inner bore, the body having an inner diameter, an outer diameter, and a length of at least approximately 20 m, wherein a standard deviation of the inner diameter is no greater than approximately 0.6% of an average inner diameter of the extruded hollow body over the length.

Item 3. The method as recited in item 2, wherein forming the silicone tube structure includes: extruding the silicone material to form an extruded member; and curing the extruded member to form the silicone tube.

Item 4. The method as recited in items 2 or 3, wherein the silicone tube structure is extruded vertically.

Item 5. The method as recited in item 4, wherein the silicone material is extruded vertically in an upward direction.

Item 6. The method as recited in any one of items 2 to 5, wherein the extrusion system includes at least one curing apparatus.

Item 7. The method as recited in item 6, wherein the at least one curing apparatus includes an infrared (IR) oven.

Item 8. The method of item 7, wherein the IR oven has a peak wavelength less than about 4 microns.

Item 9. The method as recited in any of items 2-8, wherein the extrusion system includes a gear pump coupled to an extruder.

Item 10. The method as recited in item 9, wherein the extrusion system is operated at a suction pressure with a range of 500 to 2000 psi, and at a head pressure within a range of 1000 to 4000 psi.

Item 11. The method as recited in item 9, wherein gears of the gear pump have a double helix design.

Item 12. The method as recited in any one of items 2 to 11, wherein a speed of the extrusion system is at least approximately 2 m/min, at least approximately 22 m/min, at least approximately 30 m/min, at least approximately 40 m/min, or at least approximately 50 m/min.

Item 13. The method as recited in item 2, wherein the extrusion system includes an extruder having a die and a mandrel.

Item 14. The method as recited in item 13, wherein a ratio of a land length of the die to the wall thickness of the body is no greater than approximately 6:1, no greater than approximately 5:1, or no greater than approximately 4:1.

Item 15. The method as recited in any of items 2-14, wherein the extrusion system is operated at a draw down % (DD %) within a range of about 5 to 13%, such as 5 to 10%, or 7 to 10%.

Item 16. The method as recited in any one of items 2-15, further comprising determining the outer diameter at a particular location by which the extruded hollow body passes during forming.

Item 17. The method as recited in item 16, wherein the outer diameter is determined using a laser sensor or an X-ray sensor.

Item 18. The method as recited in items 16 or 17, wherein the outer diameter at the particular location is determined at a pre-determined interval.

Item 19. The method as recited in item 18, wherein the pre-determined interval is no greater than every 0.5 seconds, no greater than every 1.5 seconds, no greater than every 5 seconds, no greater than every 10 seconds, or no greater than every 20 seconds.

Item 20. The method as recited in any one of items 9-10, further comprising adjusting a suction pressure of the extruder system based on the outer diameter of the body, adjusting a speed of the extruder system based on the outer diameter at the particular point of the body, adjusting a temperature of one or more IR ovens of the extruder system based on the outer diameter at the particular point of the body, or any combination thereof.

Item 21. The method as recited in any one of items 2 to 20, further comprising measuring one or more dimensions of the silicone tube structure before postcuring of the silicone tube structure.

Item 22. The silicone tube structure or method as recited in any one of the preceding items, wherein the standard deviation of the inner diameter is no greater than approximately 0.5% of the average inner diameter of the extruded hollow body over the length, no greater than approximately 0.4% of the average inner diameter of the extruded hollow body over the length, no greater than approximately 0.2% of the average inner diameter of the extruded hollow body over the length, or no greater than approximately 0.08% of the average inner diameter of the extruded hollow body over the length.

Item 23. The silicone tube structure or method as recited in any one of the preceding items, wherein the standard deviation of a wall thickness of the extruded hollow body is no greater than approximately 1.1% of an average wall thickness of the extruded hollow body over the length, no greater than approximately 0.8% of the average wall thickness of the extruded hollow body over the length, no greater than approximately 0.6% of the average wall thickness of the extruded hollow body over the length, no greater than approximately 0.4% of the average wall thickness of the extruded hollow body over the length, no greater than approximately 0.2% of the average wall thickness of the extruded hollow body over the length, or no greater than approximately 0.08% of the average wall thickness of the extruded hollow body over the length.

Item 24. The silicone tube structure or method as recited in any one of the preceding items, wherein a cross-section of the inner bore perpendicular to an axial direction of the body has a circular shape, a square shape, a triangular shape, or a rectangular shape.

Item 25. The silicone tube structure or method as recited in any one of the preceding items, wherein the length of the body is at least approximately 30 m, at least approximately 50 m, at least approximately 100 m, or at least approximately 125 m.

Item 26. The silicon tube structure or method as recited in any one of the preceding items, wherein the inner diameter of the body is at least approximately 2.0 mm, at least approximately 2.5 mm, or at least approximately 3.0 mm.

Item 27. The silicon tube structure or method as recited in any one of the preceding items, wherein the outer diameter of the body is at least approximately 4 mm, at least approximately 8 mm, or at least approximately 11 mm.

Item 28. The silicone tube structure or method as recited in any one of the preceding items, wherein the silicone tube comprises a polymer including a cyclic siloxane, a linear siloxane, a dimethylsiloxane, a diethylsiloxane, a diphenylsiloxane, a halosiloxane, or any combination thereof.

Item 29. The silicone tube structure or method as recited in any one of the preceding items, wherein a knit line is absent from a distal end of the body of the silicone tube and a proximal end of the body of the silicone tube.

Item 30. The silicone tube structure or method as recited in any one of the preceding items, wherein the silicone tube structure is cut into a number of silicone tubes.

Item 31. The silicone tube structure or method as recited in item 30, wherein the number of silicone tubes comprise at least a portion of a lot of tubes.

Item 32. The silicone tube structure or method as recited in any one of the preceding items, wherein the silicone tube structure comprises a plurality of lumen, each lumen of the plurality of lumen has a respective inner diameter, and the respective inner diameter of at least one lumen of the plurality of lumen has a standard deviation that is no greater than approximately 0.8% of an average inner diameter of the at least one lumen over the length.

Item 33. A lot comprising a number of silicone tubes, each silicone tube including an extruded hollow body having an inner diameter, an outer diameter, and a length, wherein a standard deviation of the inner diameter of at least approximately 95% of the number of tubes is no greater than approximately 0.6% of an average inner diameter of all of the number of tubes.

Item 34. The lot of items 33, wherein the number of silicone tubes is at least approximately 10, at least approximately 45, at least approximately 110, or at least approximately 170.

Item 35. The lot of any one of items 33 to 34, wherein the length of each silicone tube is at least approximately 8 cm, at least approximately 16 cm, or at least approximately 24 cm.

Item 36. The lot of any one of items 33 to 35, wherein the standard deviation of the inner diameter of at least approximately 97% of the number of tubes is no greater than approximately 0.6% of the average inner diameter of all of the number of tubes, the standard deviation of the inner diameter of at least approximately 99% of the number of tubes is no greater than approximately 0.6% of the average inner diameter of all of the number of tubes, the standard deviation of the inner diameter of at least approximately 99.5% of the number of tubes is no greater than approximately 0.6% of the average inner diameter of all of the number of tubes, the standard deviation of the inner diameter of at least approximately 99.9% of the number of tubes is no greater than approximately 0.6% of the average inner diameter of all of the number of tubes, or the standard deviation of the inner diameter of at least approximately 99.99% of the number of tubes is no greater than approximately 0.8% of the average inner diameter of all of the number of tubes.

Item 37. The lot of any one of items 33 to 36, wherein, a standard deviation of a wall thickness of at least approximately 95% of the number of tubes is no greater than approximately 1.1% of an average wall thickness of all of the number of tubes, the standard deviation of the wall thickness of at least approximately 97% of the number of tubes is no greater than approximately 1.1% of the average wall thickness of all of the number of tubes, the standard deviation of the wall thickness of at least approximately 99% of the number of tubes is no greater than approximately 1.1% of the average wall thickness of all of the number of tubes, the standard deviation of the wall thickness of at least approximately 99.5% of the number of tubes is no greater than approximately 1.1% of the average wall thickness of all of the number of tubes, the standard deviation of the wall thickness of at least approximately 99.9% of the number of tubes is no greater than approximately 1.1% of the average wall thickness of all of the number of tubes, or the standard deviation of the wall thickness of at least approximately 99.99% of the number of tubes is no greater than approximately 1.1% of the average wall thickness of all of the number of tubes.

Item 38. The lot of any one of items 33 to 37, wherein one or more silicone tubes of the number of silicone tubes are formed from the silicone tube structure of any one of claims 1 to 45.

Item 39. The silicone tube structure or method according to any of items 1-32, wherein the extruded hollow body has a nominal diameter of at least about 2.0 mm, such as at least about 2.5 mm, such as at least about 3.0 mm, or about 2.0 to 25.0 mm, such as 2.0 to 20.0 mm, 2.5 to 20 mm, or 3.0 to 20 mm.

Item 40. A method comprising: providing a medical device comprising a pump and a silicone tube from the number of silicone tubes according to item 30; and dispensing fluid to a patient with the medical device.

Item 41. An apparatus, comprising: a silicone tube from the number of silicone tubes according to item 30; and a pump coupled to the tube to dispense fluid contained in the tube.

Item 42. The apparatus of item 41, wherein the pump comprises a medical device to provide the fluid to a patient.

Item 43. The apparatus or method as recited in any one of items 40-42, wherein the pump is a peristaltic pump.

Item 44. The apparatus or method as recited in any one of items 40-42, wherein the pump is an infusion pump, an affinity pump, or an enteral pump.

Item 45. The apparatus or method as recited in any one of items 40-44, wherein a flow rate of the fluid is at least approximately 0.1 mL/hr., at least approximately 100 mL/hr., at least approximately 400 mL/hr., or at least approximately 700 mL/hr.

Item 46. The apparatus or method as recited in any one of items 40-45, wherein a flow rate of the fluid is no greater than approximately 1500 mL/hr., no greater than approximately 1200 mL/hr., no greater than approximately 900 mL/hr., or no greater than approximately 500 mL/hr.

The concepts described herein will be further described in the following examples, which do not limit the scope of the disclosure described in the claims.

EXAMPLES

Example 1

Silicone tubing according to Example 1 was formed using a silicone extrusion line. The extrusion line is equipped with a single-screw extruder combined with a gear pump designed for rubber. The extruder-gear pump combination is equipped with a vertical extrusion crosshead containing a tip and die with a draw down ratio (DDR) of 1.08. With a DDR of 1.08, the DD % corresponds to 8%. The extrusion line is also equipped with two IR ovens. The first (bottom) oven is a short wavelength IR oven with a peak wavelength of 1-1.2 µm (micrometers) and is set to a setting of 41 kW. The second (top) oven is a vertical, medium-to-long wavelength IR resistance-style cure oven with an IR peak wavelength between 4-7 µm (micrometers) and is set to a temperature setting of 1300° F. The extrusion line is equipped with an inline x-ray measurement system which measured the product's outer diameter, inner diameter, wall thickness, and concentricity/eccentricity. The entire extrusion line is controlled via a SCADA system (Supervisory Control and Data Acquisition) for online monitoring and automated adjustments. The tubing was produced at a rate of 120 fpm (feet per minute).

Figure 6:
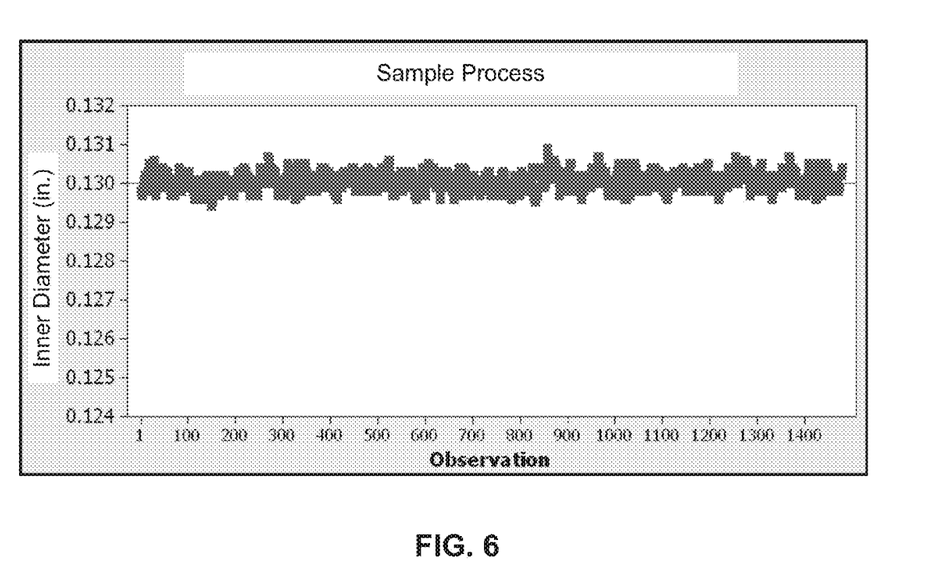
FIG. 6 is a plot of a number of measurements of the inner diameter of silicone tubing formed according to embodiments described herein.

Measurements of the inner diameter of the tubing and the wall thickness are taken by a Sikora X-ray 6035 device approximately every second during the formation of the tubing. The temperature of the room where the Sikora X-ray device is located is between approximately 68 to 72° F. The Sikora X-ray device has a resolution of approximately 5 micrometers. FIG. 6 illustrates the measurements of the inner diameter of the tubing formed according to a sample corresponding to other embodiments herein; the data reported are representative of the level of dimensional accuracy achieved according to various embodiments.

Additionally, the standard deviation of the inner diameter and wall thickness are calculated for samples of silicone tubing having particular compositions and nominal dimensions. Sample 1 is manufactured using a high consistency silicone rubber (HCR). In particular, Sample 1 is a peroxide cured polydimethylsiloxane (PDMS) silicone formulation with a Shore A durometer within a range of approximately 47 to 53 in its cured state. In its un-cured state, Sample 1 has a plasticity of 2.33 mm when tested for three minutes at 70° F. using a precision Scientific Plasticity tester per ASTM D926-80 Procedure A. Sample 2 is manufactured using a high consistency silicone rubber (HCR). In particular, Sample 2 is a platinum cured PDMS silicone formulation with a Shore A durometer within a range of approximately 47 to 53 in its cured state. In its un-cured state, Sample 2 has a plasticity of 2.16 mm when tested for three minutes at 70° F. using a Precision Scientific Plasticity tester per ASTM D926-80 Procedure A. Sample 3 is manufactured using a high consistency silicone rubber (HCR). In particular, Sample 3 is a platinum cured PDMS silicone formulation with a Shore A durometer within a range of approximately 32 to 38 in its cured state. It its un-cured state, Sample 3 has a plasticity of 1.74 mm when tested for three minutes at 70° F. using a Precision Scientific Plasticity tester per ASTM D926-80 Procedure A. The standard deviation of samples 1-3 is calculated based on 100 measurements taken over 200 feet of tubing. Table 1 indicates the nominal inner diameter for each sample, the standard deviation around the nominal inner diameter for each sample, and the percentage of the nominal inner diameter represented by the standard deviation for each respective sample. Table 2 indicates the nominal wall thickness, standard deviation for the wall thickness around the nominal wall thickness of samples 1-3, and the percentage of the nominal wall thickness represented by the standard deviation.

TABLE 1

| Name | Nominal Inner Diameter (in.) | Standard Deviation ($\sigma$) | Standard Deviation % of Nominal (%) |
| --- | --- | --- | --- |
| Sample 1 | 0.13 | 0.0002278 | 0.18% |
| Sample 2 | 0.13 | 0.0002252 | 0.17% |
| Sample 3 | 0.07 | 0.000246 | 0.35% |

TABLE 2

| Name | Nominal Wall Thickness (in.) | Standard Deviation ($\sigma$) | Standard Deviation % of Nominal (%) |
| --- | --- | --- | --- |
| Sample 1 | 0.04 | 0.0001076 | 0.27% |
| Sample 2 | 0.03 | 0.0002461 | 0.82% |
| Sample 3 | 0.04 | 0.000132 | 0.33% |

Example 2

Silicone tubing was formed using a conventional silicone extrusion line. The extrusion line is equipped with a single screw, rubber extruder equipped with a vertical extrusion crosshead containing a tip and die with a draw down ratio (DDR) of 1.01. With a DDR of 1.01, the DD % corresponds to 1%. The extrusion line is also equipped with a vertical, medium-to-long wavelength IR resistance-style cure oven with an IR peak wavelength between 4-7 μm (micrometers) and is set to a temperature setting of 1300° F. The line is equipped with an inline laser measurement system to measure the product's outer diameter. The tubing was produced at a rate of 95 fpm (feet per minute)

Figure 7:
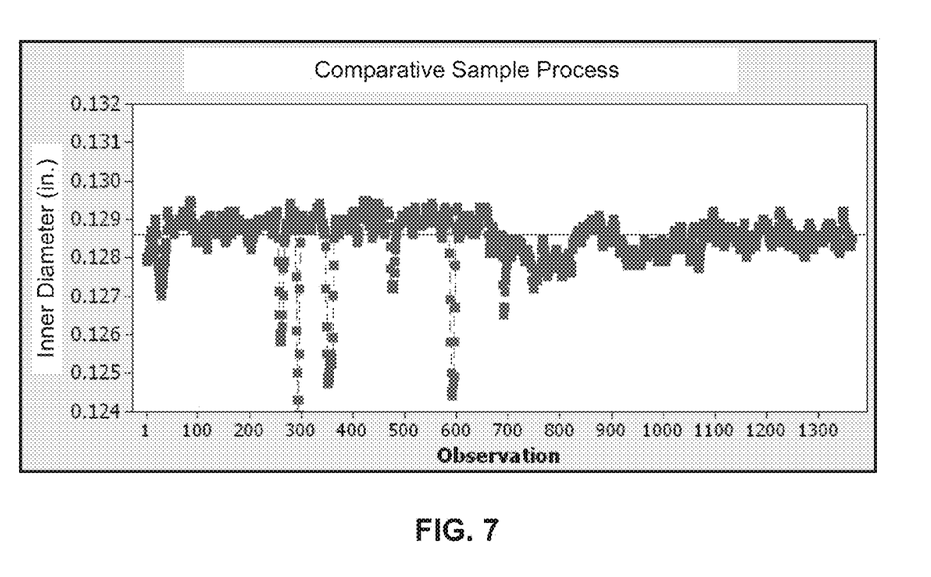
FIG. 7 is a plot of a number of measurements of the inner diameter of silicone tubing formed according to a conventional process.

Measurements of the inner diameter of the tubing and the wall thickness were taken by a Sikora X-ray device approximately every second during the formation of the tubing. The temperature of the room where the Sikora X-ray device is located is between approximately 68 to 72° F. The Sikora X-ray device has a resolution of approximately 5 micrometers. FIG. 7 illustrates the measurements of the inner diameter of the tubing.

The samples from Example 2 were found to have an inner diameter standard deviation % from nominal within a range of 0.63% to 1.7%, though some samples were higher. Those samples were also found to have a wall thickness deviation % within a range in excess of 1.1% and ranging up to 2.9%, though some samples were higher, for a 16 meter sample. However, there was a single sample that measured 0.83% for a 16 meter sample.

Further, the process capability (Cp) is calculated for the inner diameter and wall thickness for the composition of sample 1 with respect to the process used to form the silicone tubing of example 1 and the process used to form the silicone tubing of example 2 (conventional process). The $C_p$ was calculated based on a tolerance of 0.002 in. Table 3 indicates the $C_p$ for the inner diameter and wall thickness for sample 1 formed according to the process of Example 1 and Example 2.

TABLE 3

| Name | $C_p$ |
|---|---|
| Example 1 Process Inner Diameter | 3.13 |
| Example 1 Process Wall Thickness | 6.26 |
| Example 2 Process Inner Diameter | 1.23 |
| Example 2 Process Wall Thickness | 2.73 |

The higher $C_p$ values for the Example 1 process indicate that the variation of the Example 1 process is lower than that of the Example 2 process. The lower inner diameter variation for sample 1 formed according to the Example 1 process is evident through examination of FIG. 6 and FIG. 7. In particular, the variations from the nominal value that occur with many of the observations shown in FIG. 7 are absent from FIG. 6. Thus, the dimensional accuracy of silicone tubes produced by the Example 1 process is improved over that of the conventional process of Example 2.

Note that not all of the activities described above in the general description or the examples are required, that a portion of a specific activity may not be required, and that one or more further activities may be performed in addition to those described. Still further, the order in which activities are listed is not necessarily the order in which they are performed.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

The specification and illustrations of the embodiments described herein are intended to provide a general understanding of the structure of the various embodiments. The specification and illustrations are not intended to serve as an exhaustive and comprehensive description of all of the elements and features of apparatus and systems that use the structures or methods described herein. Separate embodiments may also be provided in combination in a single embodiment, and conversely, various features that are, for brevity, described in the context of a single embodiment, may also be provided separately or in any subcombination. Further, reference to values stated in ranges includes each and every value within that range. Many other embodiments may be apparent to skilled artisans only after reading this specification. Other embodiments may be used and derived from the disclosure, such that a structural substitution, logical substitution, or another change may be made without departing from the scope of the disclosure. Accordingly, the disclosure is to be regarded as illustrative rather than restrictive.

What is claimed is:

1. A silicone tube structure comprising:
   an extruded hollow body having an inner bore, the extruded hollow body having an inner diameter, an outer diameter, and a length of at least approximately 20 m;
   wherein a standard deviation of the inner diameter is no greater than approximately 0.6% of an average inner diameter of the extruded hollow body over the length.

2. The silicone tube structure as recited in claim 1, wherein the standard deviation of a wall thickness of the extruded hollow body is no greater than approximately 1.1% of an average wall thickness of the extruded hollow body over the length, no greater than approximately 0.8% of the average wall thickness of the extruded hollow body over the length, no greater than approximately 0.6% of the average wall thickness of the extruded hollow body over the length, no greater than approximately 0.4% of the average wall thickness of the extruded hollow body over the length, no greater than approximately 0.2% of the average wall thickness of the extruded hollow body over the length, or no greater than approximately 0.08% of the average wall thickness of the extruded hollow body over the length.

3. The silicone tube structure as recited in claim 1, wherein a knit line is absent from a distal end of the body of the silicone tube and a proximal end of the body of the silicone tube.

4. The silicone tube structure as recited in claim 1, wherein the silicone tube structure comprises a plurality of lumen, each lumen of the plurality of lumen has a respective inner diameter, and the respective inner diameter of at least one lumen of the plurality of lumen has a standard deviation that is no greater than approximately 0.8% of an average inner diameter of the at least one lumen over the length.

5. A method comprising:
   receiving, by an extrusion system, a silicone material; and
   forming, by the extrusion system, a silicone tube structure from the silicone material, the silicone tube structure comprising an extruded hollow body having an inner bore, the body having an inner diameter, an outer diameter, and a length of at least approximately 20 m, wherein a standard deviation of the inner diameter is no greater than approximately 0.6% of an average inner diameter of the extruded hollow body over the length.

6. The method as recited in claim 5, wherein forming the silicone tube structure includes:
   extruding the silicone material to form an extruded member; and
   curing the extruded member to form the silicone tube.

7. The method as recited in claim 5, wherein the extrusion system is operated at a draw down % (DD%) within a range of about 5 to 13%, such as 5 to 10%, or 7 to 10%.

8. The method as recited in claim 5, wherein the silicone tube structure is extruded vertically.

9. The method as recited in claim 8, wherein the silicone material is extruded vertically in an upward direction.

10. The method as recited in claim 5, wherein the extrusion system includes at least one curing apparatus.

11. The method as recited in claim 10, wherein the at least one curing apparatus includes an infrared (IR) oven.

12. The method of claim 11, wherein the IR oven has a peak wavelength less than about 4 microns.

13. The method as recited in claim 5, wherein the extrusion system includes a gear pump coupled to an extruder.

14. The method as recited in claim 13, wherein gears of the gear pump have a double helix design.

15. The method as recited in claim 13, further comprising adjusting a suction pressure of the extruder system based on the outer diameter of the body, adjusting a speed of the extruder system based on the outer diameter at the particular point of the body, adjusting a temperature of one or more IR ovens of the extruder system based on the outer diameter at the particular point of the body, or any combination thereof.

16. The method as recited in claim 5, wherein the extrusion system includes an extruder having a die and a mandrel.

17. The method as recited in claim 16, wherein a ratio of a land length of the die to the wall thickness of the body is no greater than approximately 6:1, no greater than approximately 5:1, or no greater than approximately 4:1.

18. The method as recited in claim 5, further comprising determining the outer diameter at a particular location by which the extruded hollow body passes during forming.

19. The method as recited in claim 18, wherein the outer diameter is determined using a laser sensor or an X-ray sensor.

20. A lot comprising a number of silicone tubes, each silicone tube including an extruded hollow body having an inner diameter, an outer diameter, and a length, wherein a standard deviation of the inner diameter of at least approximately 95% of the number of tubes is no greater than approximately 0.6% of an average inner diameter of all of the number of tubes; wherein the number of silicone tubes is at least approximately 10.

* * * * *